United States Patent
Tempco et al.

(10) Patent No.: US 11,191,582 B2
(45) Date of Patent: Dec. 7, 2021

(54) BONE SCREW AND METHOD OF MANUFACTURE

(71) Applicant: Warsaw Orthopedic, Inc., Warsaw, IN (US)

(72) Inventors: Dale A. Tempco, Germantown, TN (US); Rodney Ray Ballard, Lakeland, TN (US); Keith E. Miller, Germantown, TN (US); William Alan Rezach, Covington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 113 days.

(21) Appl. No.: 15/975,225

(22) Filed: May 9, 2018

(65) Prior Publication Data
US 2019/0343565 A1    Nov. 14, 2019

(51) Int. Cl.
*A61B 17/86*     (2006.01)
*B33Y 80/00*     (2015.01)

(52) U.S. Cl.
CPC .......... *A61B 17/864* (2013.01); *A61B 17/863* (2013.01); *A61B 17/866* (2013.01); *B33Y 80/00* (2014.12)

(58) Field of Classification Search
CPC ..... A61B 17/84; A61B 17/86; A61B 17/8625; A61B 17/863; A61B 17/864; A61B 17/866
See application file for complete search history.

(56) References Cited

U.S. PATENT DOCUMENTS

| | | | |
|---|---|---|---|
| 7,850,717 B2 | 12/2010 | Dewey et al. | |
| 2007/0161985 A1* | 7/2007 | Demakas | A61B 17/7032 606/274 |
| 2007/0270956 A1* | 11/2007 | Heinz | A61F 2/4455 623/17.11 |
| 2008/0177331 A1 | 7/2008 | Perez-Cruet et al. | |
| 2010/0042167 A1 | 2/2010 | Nebosky et al. | |
| 2011/0172798 A1 | 7/2011 | Staiger et al. | |
| 2012/0123485 A1 | 5/2012 | Dehnad et al. | |
| 2014/0039565 A1 | 2/2014 | Martineau et al. | |
| 2015/0018956 A1 | 1/2015 | Steinmann et al. | |
| 2015/0032159 A1 | 1/2015 | Beger et al. | |

(Continued)

FOREIGN PATENT DOCUMENTS

| CN | 104523342 A | 4/2015 |
|---|---|---|
| CN | 204337022 U | 5/2015 |

(Continued)

OTHER PUBLICATIONS

Tempco, et al., Spinal Implant and Method of Manufacture, U.S. Appl. No. 15/666,281, filed Aug. 1, 2017, 39 pages.
(Continued)

*Primary Examiner* — Eduardo C Robert
*Assistant Examiner* — Christina Negrellirodriguez
(74) *Attorney, Agent, or Firm* — Sorell, Lenna & Schmidt, LLP (57) ABSTRACT

A bone screw includes a shaft including at least one thread having an external thread form and defining at least one cavity. The shaft includes at least one tissue gathering member disposed to direct tissue into the at least one cavity. In some embodiments, systems, spinal constructs, surgical instruments and methods are disclosed.

22 Claims, 6 Drawing Sheets

(56) References Cited

U.S. PATENT DOCUMENTS

| | | |
|---|---|---|
| 2015/0223907 A1 | 8/2015 | Kieser |
| 2015/0313658 A1* | 11/2015 | Kolb .................. A61B 17/8625 606/309 |
| 2016/0157908 A1 | 6/2016 | Cawley et al. |
| 2016/0367371 A1 | 12/2016 | de Beaubien et al. |
| 2017/0165077 A1 | 6/2017 | McDonnell |
| 2017/0245851 A1 | 8/2017 | Biedermann et al. |
| 2018/0028242 A1 | 2/2018 | Parekh et al. |
| 2018/0042702 A1 | 2/2018 | Stuebinger |

FOREIGN PATENT DOCUMENTS

| | | | |
|---|---|---|---|
| CN | 204337069 U | | 5/2015 |
| CN | 104758042 A | | 7/2015 |
| CN | 104840243 A | | 8/2015 |
| CN | 204581484 U | | 8/2015 |
| CN | 204931871 U | | 1/2016 |
| CN | 204931872 U | | 1/2016 |
| CN | 105662621 A | | 6/2016 |
| CN | 205698065 U | | 11/2016 |
| CN | 106473787 A | | 3/2017 |
| CN | 106580494 A | | 4/2017 |
| CN | 106859792 A | | 6/2017 |
| CN | 206576968 U | | 10/2017 |
| CN | 206761724 U | | 12/2017 |
| CN | 206761725 U | | 12/2017 |
| CN | 206761797 U | | 12/2017 |
| CN | 206761967 U | | 12/2017 |
| FR | 3036945 A1 | | 12/2016 |
| KR | 20140141463 A | | 12/2014 |
| WO | 2014076157 A1 | | 5/2014 |
| WO | WO 2016/099620 A1 | | 6/2016 |
| WO | 2017161115 A1 | | 9/2017 |
| WO | 2017161121 A1 | | 9/2017 |
| WO | 2017192853 A1 | | 11/2017 |

OTHER PUBLICATIONS

Tempco, et al., System and Method of Manufacture for Spinal Implant, U.S. Appl. No. 15/666,305, filed Aug. 1, 2017, 39 pages.
Tempco, et al., System and Method of Manufacture for Spinal Implant, U.S. Appl. No. 15/889,355, filed Feb. 6, 2018, 41 pages.
BoneZone Magazine, Commercialization Solutions for the Orthopaedic Industry www.BONEZONEpub.com, vol. 16 Issue 3 | Aug. 2017, 2 pages.
AmorChem, Porous_screw, McGill, Research Institute McGill University Health Centre—Press Release 2012, 2 pages.
International Search Report for PCT/US2019/031268 date of completion is Aug. 26, 2019 (4 pages).

* cited by examiner

FIG. 8

BONE SCREW AND METHOD OF MANUFACTURE

TECHNICAL FIELD

The present disclosure generally relates to medical devices for the treatment of spinal disorders, and more particularly to a spinal implant system having spinal implants manufactured by a method including a plurality of manufacturing techniques.

BACKGROUND

Spinal pathologies and disorders such as kyphosis, scoliosis and other curvature abnormalities, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs including bone fasteners are often used to provide stability to a treated region. Such bone fasteners are traditionally manufactured using a medical machining technique. This disclosure describes an improvement over these prior technologies.

SUMMARY

In one embodiment, a bone screw is provided. The bone screw includes a shaft including at least one thread having an external thread form and defining at least one cavity. The shaft includes at least one tissue gathering member disposed to direct tissue into the at least one cavity. In some embodiments, systems, spinal constructs, spinal implants, surgical instruments and methods are disclosed.

In one embodiment, the bone screw comprises a shaft defining at least one cavity and including at least one thread having an external thread form. The shaft including at least one scoop configured as a tissue gathering member disposed to direct tissue into the at least one cavity.

In one embodiment, the bone screw comprises a shaft defining at least one cavity and including at least one thread having an external thread form. The shaft including at least one scoop configured as a tissue gathering member disposed to direct tissue into the at least one cavity. The thread form including a first portion defining a crest of the thread form and a second portion extending between a minor diameter of the thread form and the crest. The first portion having a solid configuration relative to the second portion.

BRIEF DESCRIPTION OF THE DRAWINGS

The present disclosure will become more readily apparent from the specific description accompanied by the following drawings, in which.

DETAILED DESCRIPTION

The exemplary embodiments of a surgical system and related methods of use disclosed are discussed in terms of medical devices for the treatment of musculoskeletal disorders and more particularly, in terms of a self-grafting spinal implant. In some embodiments, the spinal implant system includes a spinal implant comprising a self-grafting bone screw. In some embodiments, the spinal implant is manufactured via an additive manufacturing technique.

In some embodiments, the spinal implant system of the present disclosure comprises a self-grafting bone screw that combines a manufacturing method, such as, for example, one or more traditional manufacturing features and materials and a manufacturing method, such as, for example, one or more additive manufacturing features and materials. In some embodiments, the bone screw is configured for engagement with cortical and/or cancellous bone. In some embodiments, the bone screw includes structures, such as, for example, patterns, pores and/or tunnels configured to disrupt and capture cortical and/or cancellous bone during engagement. In some embodiments, the captured cortical and/or cancellous bone is embedded within the bone screw as bone graft to facilitate promotion of bone growth and bone screw fusion.

In some embodiments, the structures may be disposed along a shaft portion of bone screw. In some embodiments, the structures include a coarse surface. In some embodiments, the structures may be disposed continuously along a surface of the bone screw, such as, for example, along a distal end. In some embodiments, the structures may be disposed non-continuously along a portion of the bone screw. In some embodiments, the structures may include a bone scaffold. In some embodiments, the structures may include open voids. In some embodiments, the structures may include a cavity configured to scoop cortical and/or cancellous bone. In some embodiments, the cavity may be disposed on a minor diameter of the bone screw and/or on the screw thread. In some embodiments, the cavity may be configured as shallow or tunnel shaped cavity. In some embodiments, the cavity facilitates bone to grow therethrough.

In some embodiments, the spinal implant system of the present disclosure is configured to enhance fixation of bone screws with bone. In some embodiments, the spinal implant is configured for engagement with cortical bone and cancellous bone within the vertebra. In some embodiments, the spinal implant system of the present disclosure is configured to resist and/or prevent toggle of the bone screw resulting from a load on the bone screw when the bone screw is engaged with dense cortical bone and a less dense cancellous bone. In some embodiments, the spinal implant system of the present disclosure is configured to resist and/or prevent loosening of the bone screw from the cortical bone and in some instances, pull out from the vertebra. In some embodiments, the spinal implant system of the present disclosure is configured to self-graft to provide for an improved bone attachment to the bone screw. The bone screw is anchored in the bone thereby reducing pull out.

In some embodiments, the spinal implants system comprises a spinal implant having a hybrid configuration that combines a manufacturing method, such as, for example, one or more traditional manufacturing features and materials and a manufacturing method, such as, for example, one or more additive manufacturing features and materials. In some embodiments, additive manufacturing includes 3-D printing. In some embodiments, additive manufacturing includes fused deposition modeling, selective laser sintering, direct metal laser sintering, selective laser melting, electron beam melting, layered object manufacturing and stereolithography. In some embodiments, additive manufacturing includes rapid prototyping, desktop manufacturing, direct manufacturing, direct digital manufacturing, digital fabrication, instant manufacturing and on-demand manufacturing. In some embodiments, the spinal implant system comprises a spinal implant being manufactured by a fully additive process and grown or otherwise printed.

In some embodiments, the spinal implant system of the present disclosure comprises a spinal implant, such as, for example, a bone screw manufactured by combining traditional manufacturing methods and additive manufacturing methods. In some embodiments, the bone screw is manufactured by applying additive manufacturing material in areas where the bone screw can benefit from materials and properties of additive manufacturing. In some embodiments, traditional materials are utilized where the benefits of these materials, such as physical properties and cost, are superior to those resulting from additive manufacturing features and materials.

In some embodiments, the spinal implants, surgical instruments and/or medical devices of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the spinal implants, surgical instruments and/or medical devices of the present disclosure may be employed with other osteal and bone related applications, including those associated with diagnostics and therapeutics. In some embodiments, the spinal implants, surgical instruments and/or medical devices of the present disclosure may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions such as maxillofacial and extremities. The spinal implants, surgical instruments and/or medical devices of the present disclosure may also be alternatively employed with procedures for treating the lumbar, cervical, thoracic, sacral and pelvic regions of a spinal column. The spinal implants, surgical instruments and/or medical devices of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a spinal implant, a method of manufacturing a spinal implant such as a bone fastener, related components and methods of employing the surgical system in accordance with the principles of the present disclosure. Alternate embodiments are disclosed. Reference is made in detail to the exemplary embodiments of the present disclosure, which are illustrated in the accompanying figures. Turning to FIGS. 1-4, there are illustrated components of a spinal implant system 10 including spinal implants, surgical instruments and medical devices.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 includes a spinal implant comprising a bone fastener, such as, for example, a bone screw 12. Bone screw 12 includes a tissue gathering member to facilitate self-grafting fixation with tissue. In some embodiments, the tissue gathering member is configured to engage tissue and direct the tissue into a cavity of bone screw 12. In some embodiments, the cavity may include, such as, for example, a depression on a surface of bone screw 12, an opening and/or passageway within bone screw 12 and/or the cavity may include one or a plurality of open and/or closed sections, which may communicate.

Bone screw 12 defines a longitudinal axis X1. Bone screw 12 includes an elongated screw shaft 18 having a proximal portion 14 and a distal portion 16. In some embodiments, bone screw 12 is manufactured by a manufacturing process to enhance fixation and/or facilitate bone growth, as described herein. In some embodiments, bone screw 12 is manufactured by an additive manufacturing method. In some embodiments, proximal portion 14 is fabricated by a first manufacturing method and distal portion 16 fabricated by a second manufacturing method to enhance fixation and/or facilitate bone growth, as described herein.

In some embodiments, the manufacturing method can include a traditional machining method, such as, for example, subtractive, deformative or transformative manufacturing methods. In some embodiments, the traditional manufacturing method may include cutting, grinding, rolling, forming, molding, casting, forging, extruding, whirling, grinding and/or cold working. In some embodiments, the traditional manufacturing method includes portion 14 being formed by a medical machining process. In some embodiments, medical machining processes can include use of computer numerical control (CNC) high speed milling machines, Swiss machining devices, CNC turning with living tooling and/or wire EDM 4th axis. In some embodiments, the manufacturing method for fabricating portion 14 includes a finishing process, such as, for example, laser marking, tumble blasting, bead blasting, micro blasting and/or powder blasting.

Figure 1:
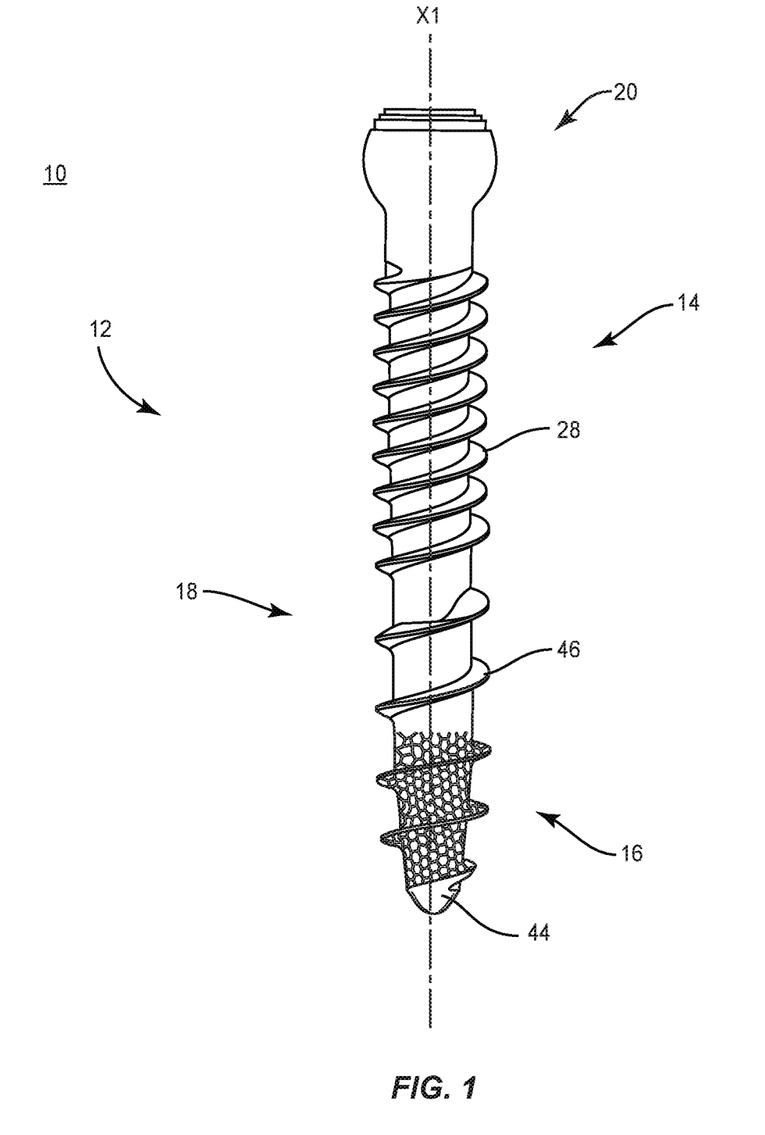
FIG. 1 is a side view of components of one embodiment of a system in accordance with the principles of the present disclosure.
Figure 2:
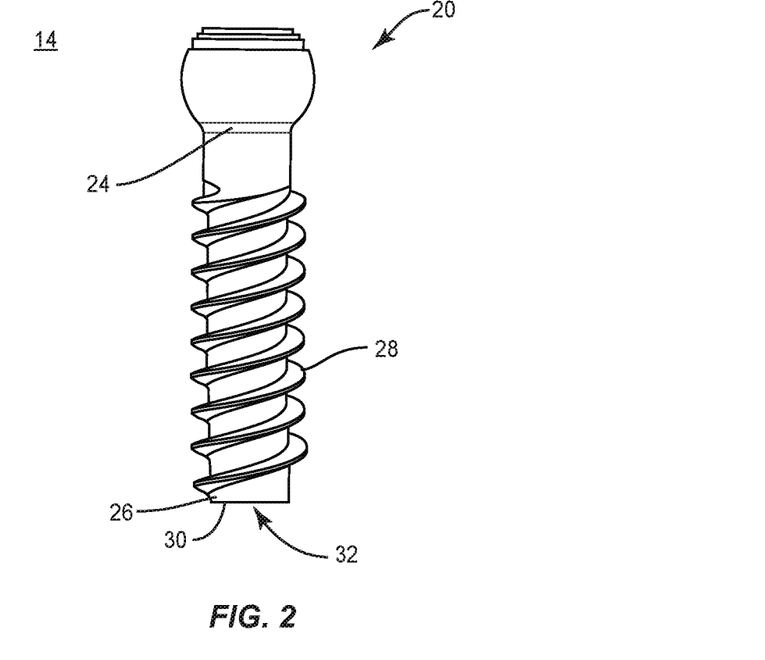
FIG. 2 is a side view of components of the system shown in FIG. 1.

For example, portion 14 is formed by a manufacturing method, which includes feeding a wire, rod, bar, or wire or rod bar stock into a machine that cuts the wire at a designated length to form a screw blank and then forms a head of the screw blank into a selected configuration. Portion 14 is manufactured to include a head 20 and a portion of screw shaft 18. Portion 14 extends between an end 24 and an end 26. End 24 includes head 20.

Portion 14 includes threads 28, which are fabricated by traditional machining methods, as described herein. Threads 28 extend along all or a portion of portion 14. Threads 28 are oriented with portion 14 and disposed for engagement with tissue. In some embodiments, threads 28 include a fine, closely-spaced configuration and/or shallow configuration to facilitate and/or enhance engagement with tissue. In some embodiments, threads 28 include a smaller pitch or more thread turns per axial distance to provide a stronger fixation with tissue and/or resist loosening from tissue. In some embodiments, threads 28 include an increased pitch and an equal lead between thread turns. In some embodiments, threads 28 are continuous along portion 14. In some embodiments, threads 28 are continuous along shaft 18 via a second manufacturing method, as described herein. In some embodiments, threads 28 may be intermittent, staggered, discontinuous and/or may include a single thread turn or a plurality of discrete threads. In some embodiments, other penetrating elements may be located on and/or manufactured with portion 14, such as, for example, a nail configuration, barbs, expanding elements, raised elements, ribs, and/or spikes to facilitate engagement of portion 14 with tissue.

End 26 includes a surface 30 that defines a distal end 32. In some embodiments, surface 30 may be disposed along a length of portion 14 or at a distalmost surface of portion 14. In some embodiments, distal end 32 extends perpendicular to axis X1. In some embodiments, distal end 32 may be disposed in various orientations relative to axis X1, such as, for example, transverse and/or at angular orientations, such as acute or obtuse. In one embodiment, distal end 32 is disposed at an acute angular orientation relative to axis X1.

Distal end 32 is configured for providing a fabrication platform for forming portion 16 thereon with an additive manufacturing method, as described herein. Distal end 32 has a substantially planar configuration for material deposition and/or heating during an additive manufacturing process for fabricating portion 16 onto distal end 32. In some embodiments, all or only a portion of distal end 32 may have alternate surface configurations, such as, for example, angled, irregular, uniform, non-uniform, offset, staggered, tapered, arcuate, undulating, mesh, porous, semi-porous, dimpled, pointed and/or textured. In some embodiments, distal end 32 may include a nail configuration, barbs, expanding elements, raised elements, ribs, and/or spikes to provide a fabrication platform for forming portion 16 thereon with an additive manufacturing method, as described herein. In some embodiments, all or only a portion of distal end 32 may have alternate cross section configurations, such as, for example, oval, oblong triangular, square, polygonal, irregular, uniform, non-uniform, offset, staggered, and/or tapered.

Portion 16 is fabricated with a second manufacturing method by disposing a material onto distal end 32, as described herein. Portion 16 is configured for fabrication on distal end 32 such that portion 16 is fused with surface 30. Portion 16 is formed on distal end 32 by an additive manufacturing method. Portion 16 is formed on distal end 32 to extend between an end 40 and end 42 according to instructions received from the computer and processor, and end 40 is fused with surface 30. End 42 includes a distal tip 44.

Figure 3:
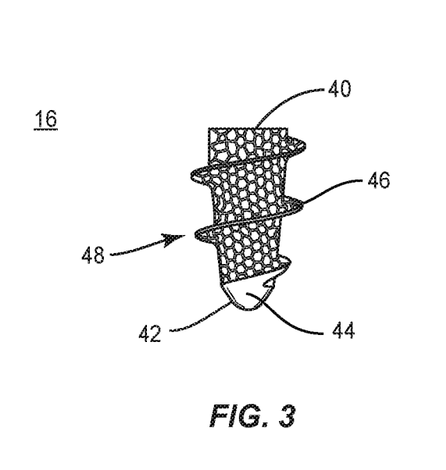
FIG. 3 is a side view of components of the system shown in FIG. 1.

Portion 16 is fabricated according to instructions received from the computer and processor based on the digital rendering and/or data of the selected configuration, via the additive manufacturing process described herein to include a thread 46 that extends between end 40 and distal tip 44. Thread 46 includes an external thread form 48. In some embodiments, thread 46 is fabricated to include a fine, closely-spaced and/or shallow configuration to facilitate and/or enhance engagement with tissue. In some embodiments, thread 46 is fabricated to include an increased pitch and an equal lead between thread turns than thread 28, as shown in FIG. 1. In some embodiments, thread 46 is fabricated to include a smaller pitch or more thread turns per axial distance than thread 28 to provide a stronger fixation with tissue and/or resist loosening from tissue. In some embodiments, thread 46 is fabricated to be continuous along portion 16. In some embodiments, thread 46 is fabricated to be continuous along portion 16. In some embodiments, thread 46 is fabricated to be intermittent, staggered, discontinuous and/or may include a single thread turn or a plurality of discrete threads. In some embodiments, portion 16 is fabricated to include penetrating elements, such as, for example, a nail configuration, barbs, expanding elements, raised elements, ribs, and/or spikes. In some embodiments, thread 46 is fabricated to be self-tapping or intermittent at distal tip 44. In some embodiments, distal tip 44 may be rounded. In some embodiments, distal tip 44 may be self-drilling. In some embodiments, distal tip 44 includes a solid outer surface, as shown in FIGS. 1 and 3.

Portion 16 includes a wall 50 having a surface 52. In some embodiments, wall 50 extends circumferentially to define portion 16. In some embodiments, wall 50 defines a thickness, which may be uniform, undulating, tapered, increasing, decreasing, variable, offset, stepped, arcuate, angled and/or staggered. In some embodiments, surface 52 may be rough, textured, porous, semi-porous, dimpled, knurled, toothed, grooved and/or polished. In some embodiments, wall 50 defines a cavity extending therein. In some embodiments, surface 52 of wall 50 defines one or a plurality of cavities.

Surface 52 includes at least one tissue gathering member, such as, for example, a lattice 56. In some embodiments, surface 52 includes a non-solid configuration, which may include a porous structure and/or a trabecular configuration. Disclosures herein involving a lattice, or other particular type of non-solid structure, are meant to disclose at the same time analogous embodiments in which other non-solid structure in addition or instead of the particular type of structure.

In various embodiments, the non-solid configuration is configured to provide one or a plurality of pathways to facilitate bone through growth within, and in some embodiments all of the way through, from one surface to an opposite surface of bone screw 12. Lattice 56 is continuous along surface 52 of portion 16 between end 40 and distal tip 44. Thread 46 is connected with lattice 56 to facilitate fixation of threads 46 with tissue. In some embodiments, lattice 56 may include one or more portions, layers and/or substrates. In some embodiments, one or more portions, layers and/or substrates of lattice 56 may be disposed side by side, offset, staggered, stepped, tapered, end to end, spaced apart, in series and/or in parallel. In some embodiments, lattice 56 defines a thickness, which may be uniform, undulating, tapered, increasing, decreasing, variable, offset, stepped, arcuate, angled and/or staggered. In some embodiments, one or more layers of lattice 56 are disposed in a side by side, parallel orientation within the cavity and wall 50. Lattice 56 includes one or more layers of a matrix of material, such as, for example, a latticework 60. Latticework 60 includes a plurality of nodes 64 and openings 66 disposed in rows and columns and/or in series and parallel.

Figure 4:
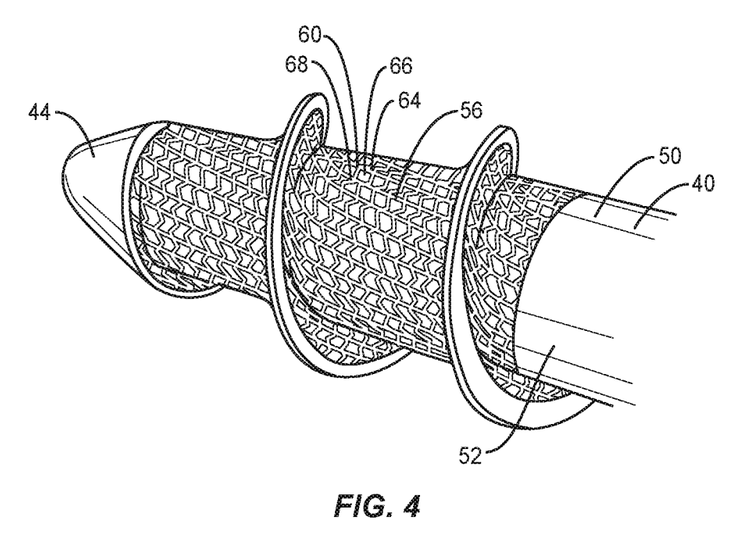
FIG. 4 is a perspective view of the components of the system shown in FIG. 3.

Lattice 56 includes surfaces 68 disposed with nodes 64, as shown in FIG. 4. In some embodiments, surfaces 68 may form a rasp-like configuration. Surfaces 68 are configured to engage tissue, such as, for example, cortical bone and/or cancellous bone, such as, to cut, shave, shear, incise and/or disrupt such tissue. In some embodiments, all or a portion of each surface 68 may have various configurations, such as, for example, cylindrical, round, oval, oblong, triangular, polygonal having planar or arcuate side portions, irregular, uniform, non-uniform, consistent, variable, horseshoe shape, U-shape or kidney bean shape. In some embodiments, surface 68 may be rough, textured, porous, semi-porous, dimpled, knurled, toothed, grooved and/or polished to facilitate engagement and cutting of tissue. Surfaces 68 form a tunnel configured to guide, drive and/or direct the cut tissue into the cavity to facilitate fusion of bone screw 12 with tissue, such as, for example, vertebrae. Manipulation of bone screw 12, including rotation and/or translation, causes surfaces 68 to disrupt, scrape, cut and/or remove tissue at a surgical site and guide the cut tissue into the cavity and/or openings 66. The tissue becomes imbedded into the cavity and/or openings 66 to promote bone growth to enhance fusion of bone screw 12. In some embodiments, external grating materials or biologics may be prepacked with bone screw 12.

In some embodiments, additive manufacturing includes 3-D printing, as described herein. In some embodiments, additive manufacturing includes fused deposition modeling, selective laser sintering, direct metal laser sintering, selective laser melting, electron beam melting, layered object manufacturing and stereolithography. In some embodiments, additive manufacturing includes rapid prototyping, desktop manufacturing, direct manufacturing, direct digital manufacturing, digital fabrication, instant manufacturing or on-demand manufacturing. In some embodiments, portion 16 is manufactured by additive manufacturing, as described herein, and mechanically attached with surface 30 by, for example, welding, threading, adhesives and/or staking.

In one embodiment, one or more manufacturing methods for fabricating distal portion 16, proximal portion 14 and/or other components of bone screw 12 include imaging patient anatomy with imaging techniques, such as, for example, x-ray, fluoroscopy, computed tomography (CT), magnetic resonance imaging (MRI), surgical navigation, bone density (DEXA) and/or acquirable 2-D or 3-D images of patient anatomy. Selected configuration parameters of distal portion 16, proximal portion 14 and/or other components of bone screw 12 are collected, calculated and/or determined. Such configuration parameters can include one or more of patient anatomy imaging, surgical treatment, historical patient data, statistical data, treatment algorithms, implant material, implant dimensions, porosity and/or manufacturing method. In some embodiments, the configuration parameters can include implant material and porosity of distal portion 16 determined based on patient anatomy and the surgical treatment. In some embodiments, the implant material includes a selected porosity of distal portion 16, as described herein. In some embodiments, the selected configuration parameters of distal portion 16, proximal portion 14 and/or other components of bone screw 12 are patient specific. In some embodiments, the selected configuration parameters of distal portion 16, proximal portion 14 and/or other components of bone screw 12 are based on generic or standard configurations and/or sizes and not patient specific. In some embodiments, the selected configuration parameters of distal portion 16, proximal portion 14 and/or other components of bone screw 12 are based on one or more configurations and/or sizes of components of a kit of spinal implant system 10 and not patient specific.

For example, based on one or more selected configuration parameters, as described herein, a digital rendering and/or data of a selected distal portion 16, proximal portion 14 and/or other components of bone screw 12, which can include a 2-D or a 3-D digital model and/or image, is collected, calculated and/or determined, and generated for display from a graphical user interface, as described herein, and/or storage on a database attached to a computer and a processor (not shown), as described herein. In some embodiments, the computer provides the ability to display, via a monitor, as well as save, digitally manipulate, or print a hard copy of the digital rendering and/or data. In some embodiments, a selected distal portion 16, proximal portion 14 and/or other components of bone screw 12 can be designed virtually in the computer with a CAD/CAM program, which is on a computer display. In some embodiments, the processor may execute codes stored in a computer-readable memory medium to execute one or more instructions of the computer, for example, to transmit instructions to an additive manufacturing device, such as, for example, a 3-D printer. In some embodiments, the database and/or computer-readable medium may include RAM, ROM, EPROM, magnetic, optical, digital, electromagnetic, flash drive and/or semiconductor technology. In some embodiments, the processor can instruct motors (not shown) that control movement and rotation of spinal implant system 10 components, for example, a build plate 200, distal end 32 and/or laser emitting devices, as described herein.

Portion 14 is fabricated with threads 28 by a first manufacturing method, as described herein. Portion 14 is connected with a part, such as, for example, a build plate in connection with an additive forming process and a second manufacturing method for fabricating distal portion 16. Portion 16 is built up layer by layer and the melting process is repeated slice by slice, layer by layer, until the final layer of material is melted and portion 16 is complete, as shown in FIG. 15. Portion 16 is formed on distal end 32 to extend between an end 40 and an end 42 according to instructions received from the computer and processor, and end 40 is fused with surface 30. End 42 includes a distal tip 44. In some embodiments, material M is subjected to direct metal laser sintering (DMLS®), selective laser sintering (SLS), fused deposition modeling (FDM), or fused filament fabrication (FFF), or stereolithography (SLA).

In some embodiments, portion 16 is fabricated in a configuration having a porosity via the additive manufacturing method, as described herein. In some embodiments, portion 16 is fabricated having a porosity with a porogen that is spheroidal, cuboidal, rectangular, elongated, tubular, fibrous, disc-shaped, platelet-shaped, polygonal or a mixture thereof. In some embodiments, a porosity of portion 16 is based on a plurality of macropores, micropores, nanopores structures and/or a combination thereof.

In some embodiments, bone screw 12 includes an implant receiver (not shown) connectable with head 20. In some embodiments, bone screw 12 can include various configurations, such as, for example, a posted screw, a pedicle screw, a bolt, a bone screw for a lateral plate, an interbody screw, a uni-axial screw, a fixed angle screw, a multi-axial screw, a side loading screw, a sagittal adjusting screw, a transverse sagittal adjusting screw, an awl tip, a dual rod multi-axial screw, midline lumbar fusion screw and/or a sacral bone screw. In some embodiments, the implant receiver can be attached by manual engagement and/or non-instrumented assembly, which may include a practitioner, surgeon and/or medical staff grasping the implant receiver and shaft 18 and forcibly snap or pop fitting the components together. In some embodiments, spinal implant system 10 comprises a kit including a plurality of bone screws 12 of varying configuration, as described herein. In some embodiments, bone screw 12 is selected from the kit and employed with a treatment at the surgical site.

In one embodiment, bone screw 12 is fabricated to define a passageway through all or a portion of shaft 18 such that bone screw 12 includes a cannulated configuration and a plurality of lateral fenestrations in communication with the passageway.

In assembly, operation and use, spinal implant system 10 is employed to treat an affected section of vertebrae. A medical practitioner obtains access to a surgical site including the vertebrae in any appropriate manner, such as through incision and retraction of tissues. The components of surgical system 10 including bone screw 12 are employed to augment a surgical treatment. Bone screw 12 can be delivered to a surgical site as a pre-assembled device or can be assembled in situ. Spinal implant system 10 may be may be completely or partially revised, removed or replaced.

Surgical system 10 may be used with surgical methods or techniques including open surgery, mini-open surgery, minimally invasive surgery and percutaneous surgical implantation, whereby the vertebrae is accessed through a mini-incision, or sleeve that provides a protected passageway to the area. Once access to the surgical site is obtained, a surgical treatment, for example, corpectomy and/or discectomy, can be performed for treating a spine disorder.

Bone screw 12 is connected with a surgical instrument, such as, for example, a driver (not shown) and is delivered to the surgical site. Bone screw 12 is manipulated including rotation and/or translation for engagement with cortical bone and/or cancellous bone. Surfaces 68 cut, shave, shear, incise and/or disrupt the bone tissue. Surfaces 68 guide, drive and/or direct the cut tissue into the cavity and/or openings 66 to facilitate fusion of bone screw 12 with tissue. The tissue becomes imbedded into the cavity and/or openings 66 to promote bone growth and enhance fusion of bone screw 12 to resist and/or prevent toggle.

Figure 5:
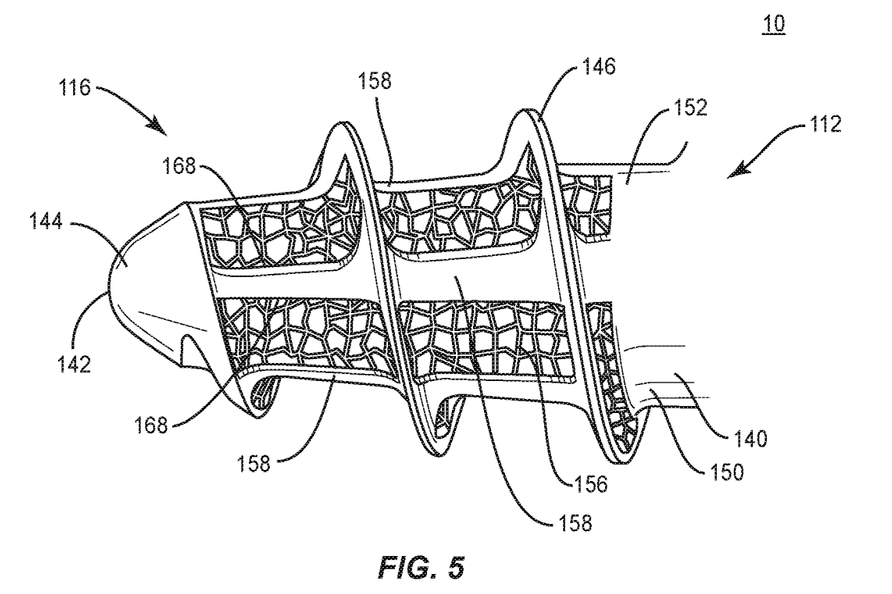
FIG. 5 is a perspective view of components of one embodiment of a system in accordance with the principles of the present disclosure.

In one embodiment, as shown in FIG. 5, spinal implant system 10, similar to the systems and methods described herein, includes a bone screw 112, similar to bone screw 12 described herein. Bone screw 112 includes portion 14, as described herein, and a portion 116. Portion 116 extends between an end 140 and an end 142. End 142 includes a distal tip 144. Portion 116 includes a thread 146 that extends between end 140 and distal tip 144.

Portion 116 includes a wall 150 having a surface 152. Wall 150 includes a plurality of struts 158 that extend between end 140 and distal tip 144. Struts 158 are circumferentially disposed about portion 116 and define a cavity therebetween. Struts 158 are configured to increase the mechanical strength of bone screw 112. In some embodiments, struts 158 are configured to provide additional strength to distal tip 144. A lattice 156, similar to lattice 56 described herein, is disposed with the cavity such that lattice 156 is non-continuous along portion 116. Thread 146 is connected with struts 158. Struts 158 includes edges 168, similar to surfaces 68 described herein, configured to engage tissue to cut, shave, shear, incise and/or disrupt such tissue. Manipulation of bone screw 112, including rotation and/or translation, causes edges 168 to disrupt, scrape, cut and/or remove tissue at a surgical site and guide the cut tissue into the cavity. The tissue becomes imbedded into the cavity and promotes bone growth to enhance fusion of bone screw 112.

In some embodiments, portion 116 is formed on distal end 32 by an additive manufacturing method, as described herein. In some embodiments, portion 116 is fabricated according to instructions received from the computer and processor based on the digital rendering and/or data of the selected configuration, via the additive manufacturing process, as described herein. Portion 116 is configured for fabrication on distal end 32 such that portion 116 is fused with surface 30, as described herein.

Figure 6:
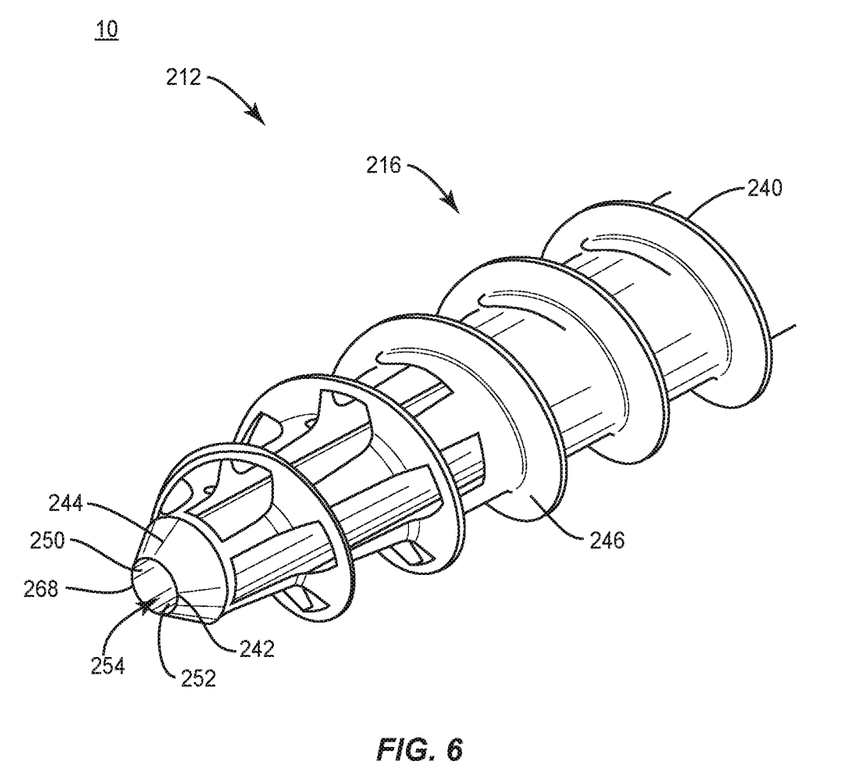
FIG. 6 is a perspective view of components of one embodiment of a system in accordance with the principles of the present disclosure.

In one embodiment, as shown in FIG. 6, spinal implant system 10, similar to the systems and methods described herein, includes a bone screw 212, similar to bone screw 12 described herein. Bone screw 212 includes portion 14, as described herein, and a portion 216. Portion 216 extends between an end 240 and an end 242. End 242 includes a distal tip 244. Portion 216 includes a thread 246 that extends between end 240 and distal tip 244.

Portion 216 includes a wall 250 having an inner surface 252. Surface 252 defines a longitudinal cavity 254. Wall 250 includes a distal cutting face 268 disposed at a distal end of portion 216. Cutting face 268 is configured to engage tissue to cut, shave, shear, incise and/or disrupt such tissue. Manipulation of bone screw 212, including rotation and/or translation, causes cutting face 268 to disrupt, scrape, cut and/or remove tissue at a surgical site and guide the cut tissue into cavity 254. The tissue becomes imbedded into cavity 254 and promotes bone growth to enhance fusion of bone screw 212.

In some embodiments, portion 216 is formed on distal end 32 by an additive manufacturing method, as described herein. In some embodiments, portion 216 is fabricated according to instructions received from the computer and processor based on the digital rendering and/or data of the selected configuration, via the additive manufacturing process, as described herein. Portion 216 is configured for fabrication on distal end 32 such that portion 216 is fused with surface 30, as described herein.

Figure 7:
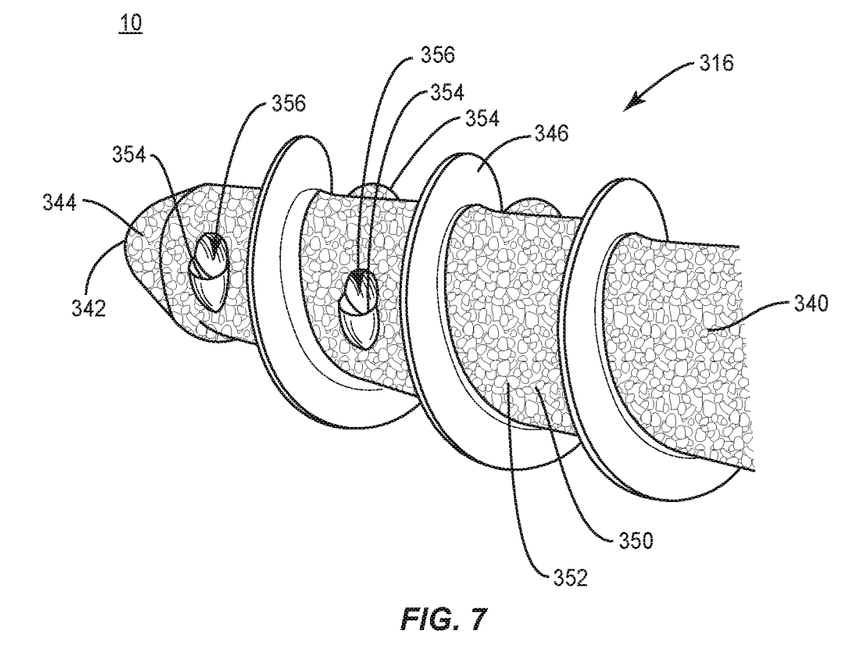
FIG. 7 is a perspective view of components of one embodiment of a system in accordance with the principles of the present disclosure.
Figure 8:
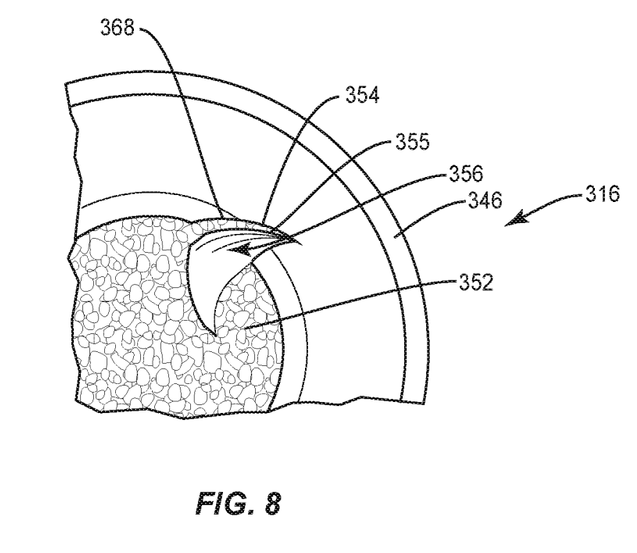
FIG. 8 is an enlarged view, part schematic cross section, of components of the system shown in FIG. 7.

In one embodiment, as shown in FIGS. 7 and 8, spinal implant system 10, similar to the systems and methods described herein, includes a bone screw 312, similar to bone screw 12 described herein. Bone screw 312 includes portion 14, as described herein, and a portion 316. Portion 316 extends between an end 340 and an end 342. End 342 includes a distal tip 344. Portion 316 includes a thread 346 that extends between end 340 and distal tip 344.

Portion 316 includes a wall 350 having a surface 352. Surface 352 defines at least one scoop 354, as shown in FIG. 7. Scoop 354 includes walls 355. Walls 355 define a cavity 356 configured for disposal of cut tissue. In some embodiments, all or only a portion of scoop 354 may have various cross section configurations, such as, for example, oval, oblong triangular, square, polygonal, irregular, uniform, non-uniform, offset, staggered, and/or tapered.

In some embodiments, scoop 354 is disposed along wall 350. In some embodiments, scoop 354 is disposed with wall 350 and/or with all or a portion of thread 346. In some embodiments, scoop 354 is disposed adjacent to and/or on a leading edge surface of thread 346, as shown in FIG. 8. In some embodiments, scoop 354 is disposed adjacent to and/or on a trailing edge surface of thread 346. In some embodiments, scoop 354 is disposed in communication with thread 346. In some embodiments, the walls of scoop 354 is not fully solid, or is non-solid, such as by having a lattice configuration. By way of example, and for clearly illustrating scoop 354, two example scoops are shown in FIG. 7, on the front side of the view, having a solid wall. And two scoops, on a back side of the view, are shown having a non-solid wall. Scoops 354 can be fully solid, or partially or fully non-solid, such as by including lattice, trabecular, or other non-solid structure. In some embodiments, surface 352 defines a plurality of scoops 354 disposed circumferentially about portion 316.

Scoop 354 includes a cutting surface 368, including a leading edge. Surface 368 is configured to engage tissue to cut, shave, shear, incise and/or disrupt such tissue. Manipulation of bone screw 312, including rotation and/or translation, causes surface 368 to disrupt, scrape, cut and/or remove tissue at a surgical site and guide the cut tissue into cavity 356. The tissue becomes imbedded into cavity 356 and promotes bone growth to enhance fusion of bone screw 312. In some embodiments, bone screw 312 has one or more voids or compartments adjacent the scoop 354, so that at least some of the tissue caused to enter the scoop is pushed, by subsequently cut tissue, into the void or compartment(s).

In some embodiments, portion 316 is formed on distal end 32 by an additive manufacturing method, as described herein. In some embodiments, portion 316 is fabricated according to instructions received from the computer and processor based on the digital rendering and/or data of the selected configuration, via the additive manufacturing process, as described herein. Portion 316 is configured for fabrication on distal end 32 such that portion 316 is fused with surface 30, as described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone screw comprising:
   a shaft defining at least one cavity and including a surface and an external thread form, the thread form comprising a root and a crest opposite the root, the root extending from the surface, the surface being made of a first material and the thread form being made of a second material, the first material having a porosity greater than a porosity of the second material, the at least one cavity extending into the surface such that the at least one cavity is spaced apart from the thread form, the shaft including a member disposed to direct tissue into the at least one cavity, the member extending from the surface, the member being positioned between adjacent threads of the thread form.

2. A bone screw as recited in claim 1, wherein the member is a tissue gathering member including at least one scoop, the at least one scoop comprising an inner wall defining at least a portion of the at least one cavity.

3. A bone screw as recited in claim 2, wherein the at least one scoop is spaced apart from threads of the thread form.

4. A bone screw as recited in claim 2, wherein the at least one scoop includes an outer wall extending outwardly from the surface.

5. A bone screw as recited in claim 2, wherein the at least one scoop includes walls having a lattice configuration.

6. A bone screw as recited in claim 1, wherein the member is a tissue gathering member including a plurality of scoops disposed circumferentially about a distal portion of the shaft, the scoops each including a wall defining a portion of the at least one cavity.

7. A bone screw as recited in claim 1, wherein the member is a tissue gathering member including a lattice.

8. A bone screw as recited in claim 7, wherein the member is a tissue gathering member including at least one scoop, the at least one scoop comprising an inner wall defining at least a portion of the at least one cavity, walls of the at least one scoop including the lattice.

9. A bone screw as recited in claim 1, wherein walls of the member include a lattice.

10. A bone screw as recited in claim 1, wherein the member is free of struts.

11. A bone screw as recited in claim 1, wherein the member is a tissue gathering member including a first scoop, the first scoop comprising an inner wall defining at least a portion of the at least one cavity, the bone screw comprising a second scoop configured to direct tissue into a second cavity.

12. A bone screw as recited in claim 11, wherein the second cavity extends into the surface.

13. A bone screw as recited in claim 11, wherein walls of the scoops each have a lattice configuration.

14. A bone screw as recited in claim 11, wherein the first scoop includes a solid wall and the second scoop comprises a non-solid wall.

15. A bone screw as recited in claim 14, wherein the first scoop is fully solid and the second scoop is fully non-solid.

16. A bone screw as recited in claim 1, wherein at least a portion of the shaft is fabricated from an additive manufacturing method including adding a material in a layer by layer formation.

17. A bone screw as recited in claim 1, wherein the member is disposed along a portion of the thread.

18. A bone screw as recited in claim 1, wherein the member is formed partially on one of the threads.

19. A bone screw as recited in claim 1, wherein the member includes a scoop comprising an inner wall defining at least a portion of the at least one cavity, the scoop including an outer wall extending outwardly from the surface, a surface of the inner wall being continuous with a surface of the outer wall.

20. A bone screw comprising:
a shaft defining at least one cavity and including a surface and an external thread form, the thread form comprising a root and a crest opposite the root, the root extending from the surface, the surface being made of a first material and the thread form being made of a second material, the first material having a porosity greater than a porosity of the second material, the at least one cavity extending into the surface such that the at least one cavity is spaced apart from the thread form, the shaft including at least one scoop configured as a member disposed to direct tissue into the at least one cavity, the at least one scoop being positioned between adjacent threads of the thread form.

21. A bone screw as recited in claim 20, wherein the at least one scoop includes a plurality of scoops disposed circumferentially about a distal portion of the shaft, the scoops each being spaced apart from threads of the thread form.

22. A bone screw comprising:
a shaft defining at least one cavity and including a surface and an external thread form, the thread form comprising a root and a crest opposite the root, the root extending from the surface, the surface being made of a first material and the thread form being made of a second material, the second material being different than the first material, the first material having a porosity greater than a porosity of the second material, the at least one cavity extending into the surface such that the at least one cavity is spaced apart from the thread form, the shaft including at least one scoop configured as a tissue gathering member disposed to direct tissue into the at least one cavity, the at least one scoop being positioned between spaced apart from threads of the thread form, the surface and the at least one scoop each having a lattice configuration.

* * * * *